United States Patent
Geshel

(10) Patent No.: US 8,640,060 B2
(45) Date of Patent: Jan. 28, 2014

(54) METHOD OF GENERATING A RECIPE FOR A MANUFACTURING TOOL AND SYSTEM THEREOF

(75) Inventor: Mark Geshel, Kfar-Saba (IL)

(73) Assignee: Applied Materials Israel, Ltd., Rehovot (IL)

( * ) Notice: Subject to any disclaimer, the term of this patent is extended or adjusted under 35 U.S.C. 154(b) by 0 days.

(21) Appl. No.: 13/482,955

(22) Filed: May 29, 2012

(65) Prior Publication Data

US 2013/0326443 A1 Dec. 5, 2013

(51) Int. Cl.
*G06F 17/50* (2006.01)

(52) U.S. Cl.
USPC .......... 716/54; 716/50; 716/51; 716/52; 716/53; 716/55; 430/5; 430/30

(58) Field of Classification Search
USPC .......... 716/50–55; 430/5, 30; 382/144
See application file for complete search history.

(56) References Cited

U.S. PATENT DOCUMENTS

| | | | | |
|---|---|---|---|---|
| 6,042,971 A | * | 3/2000 | Tamura et al. | 430/5 |
| 6,486,066 B2 | * | 11/2002 | Cleeves et al. | 438/692 |
| 6,886,153 B1 | * | 4/2005 | Bevis | 716/51 |
| 7,096,086 B2 | * | 8/2006 | Sato | 700/108 |
| 7,869,643 B2 | * | 1/2011 | Litichever et al. | 382/145 |
| 2013/0066454 A1 | * | 3/2013 | Geshel et al. | 700/97 |

* cited by examiner

*Primary Examiner* — Nghia Doan

(74) *Attorney, Agent, or Firm* — Lowenstein Sandler LLP

(57) ABSTRACT

There is provided a computer-implemented method of creating a recipe for a manufacturing tool and a system thereof. The method comprises: upon obtaining data characterizing periodical sub-arrays in one or more dies, generating candidate stitches; identifying one or more candidate stitches characterized by periodicity characteristics satisfying, at least, a periodicity criterion, thereby identifying periodical stitches among the candidate stitches; and aggregating the identified periodical stitches and the periodical sub-arrays into periodical arrays, said periodical arrays to be used for automated recipe creation.

16 Claims, 15 Drawing Sheets

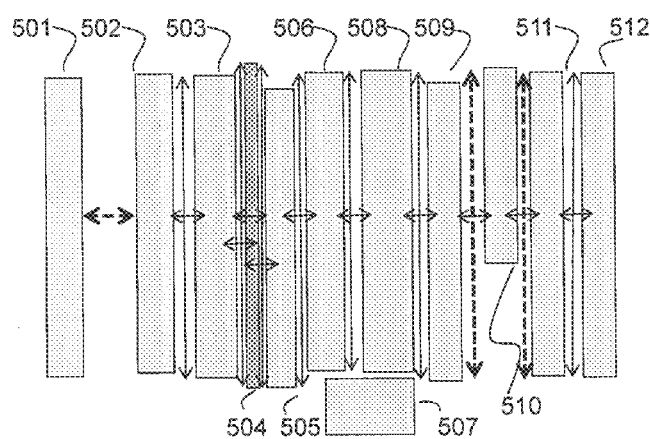
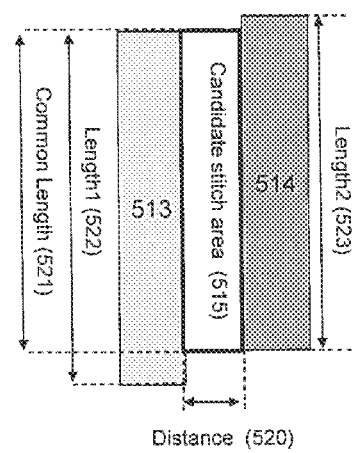
Figure 5a
Figure 5b
- Array area with Cs=Cy
- Array area with Cs=2*Cy
- ⟷ Proximity conditions okay
- ⟷ Proximity conditions failed

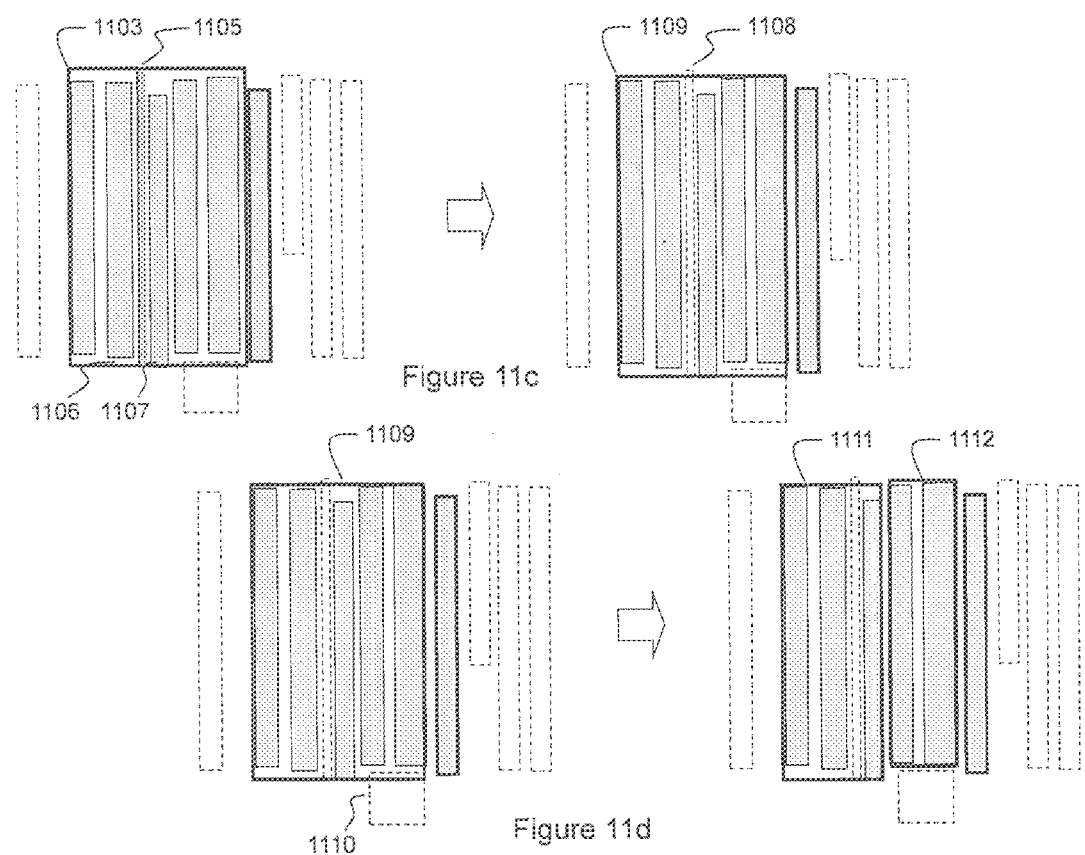

METHOD OF GENERATING A RECIPE FOR A MANUFACTURING TOOL AND SYSTEM THEREOF

FIELD OF THE INVENTION

The presently disclosed subject matter relates, in general, to methods and systems for specimen manufacturing processes and, more particularly, to methods and systems of automated recipe generation using design data.

BACKGROUND OF THE INVENTION

In the semiconductor industry, devices are fabricated by a number of manufacturing processes producing structures of an ever-decreasing size. Thus, manufacturing processes, such as inspection, metrology, and review processes require increased precision and effectiveness for manufacturing specimens. The term "specimen" used in this specification should be expansively construed to cover any kind of wafer, reticle and other structures, combinations and/or parts thereof used for manufacturing semiconductor integrated circuits, magnetic heads, flat panel displays, and other thin film devices.

Manufacturing processes, such as inspection, metrology, and review of specimens, can include recognition of structural elements, measuring, calibration, monitoring, inspection, review and analyses of defects, reporting and/or other procedures necessary for evaluating parameters and/or conditions of respective manufacturing processes and providing necessary feedback. A variety of manufacturing tools can be based on non-destructive observations as, by way of non-limiting example, scanning electron microscopes, atomic force microscopes, optical inspection tools and others, and used for inspection, metrology, and review processes. As manufacture control requirements become more challenging, recipe generation for processes, such as inspection, metrology and review processes, has also become highly complex.

The volume of measurements and the complexity of recipes in state-of-the-art specimen manufacturing have made the conventional manual (or semi-manual) process of creating the recipes increasingly problematic. Emerging techniques of automated recipe generation can improve production time and development, and reduce chances of errors.

Problems of automated recipe generation have been recognized in the conventional art and various systems have been developed to provide solutions. For example, a conventional system for creating an inspection recipe includes an inspection target selection module selecting an inspection target; a critical area extraction module extracting corresponding critical areas for defect sizes in the inspection target; a defect density prediction module extracting corresponding defect densities predicted by defects to be detected in the inspection target for the defect sizes; a killer defect calculation module calculating corresponding numbers of killer defects in the defect sizes based on the critical areas and the defect densities; and a detection expectation calculation module calculating the number of killer defects expected to be detected for prospective inspection recipes determining rates of defect detection for the defect sizes, based on the number of killer defects and the rates of defect detection prescribed in the prospective inspection recipes.

Another conventional method for creating an inspection recipe includes acquiring a first design and one or more characteristics of output of an inspection system for a wafer on which the first design is printed using a manufacturing process. The method also includes creating an inspection recipe for a second design using the first design and the one or more characteristics of the output acquired for the wafer on which the first design is printed. The first and second designs are different. The inspection recipe is used for inspecting wafers after the second design is printed on the wafers using the manufacturing process.

Another conventional recipe generations solutions generate recipes based on wafers that have been produced. Traditional solutions rely on a first wafer to be manufactured, and comprise capturing an image of the wafer, examining the produced wafer, and generating a recipe based on analysis of the examined wafer.

BRIEF DESCRIPTION OF THE DRAWINGS

The presently disclosed subject matter is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIGS. 5a-5b illustrate a non-limiting schematic example of an initial die layout for Y direction inspection/review in accordance with certain embodiments of the presently disclosed subject matter;

FIGS. 11a-11f illustrate non-limiting schematic examples of aggregating steps provided for the exemplarily initial layout illustrated in FIG. 5a;

SUMMARY OF THE INVENTION

Figure 1:
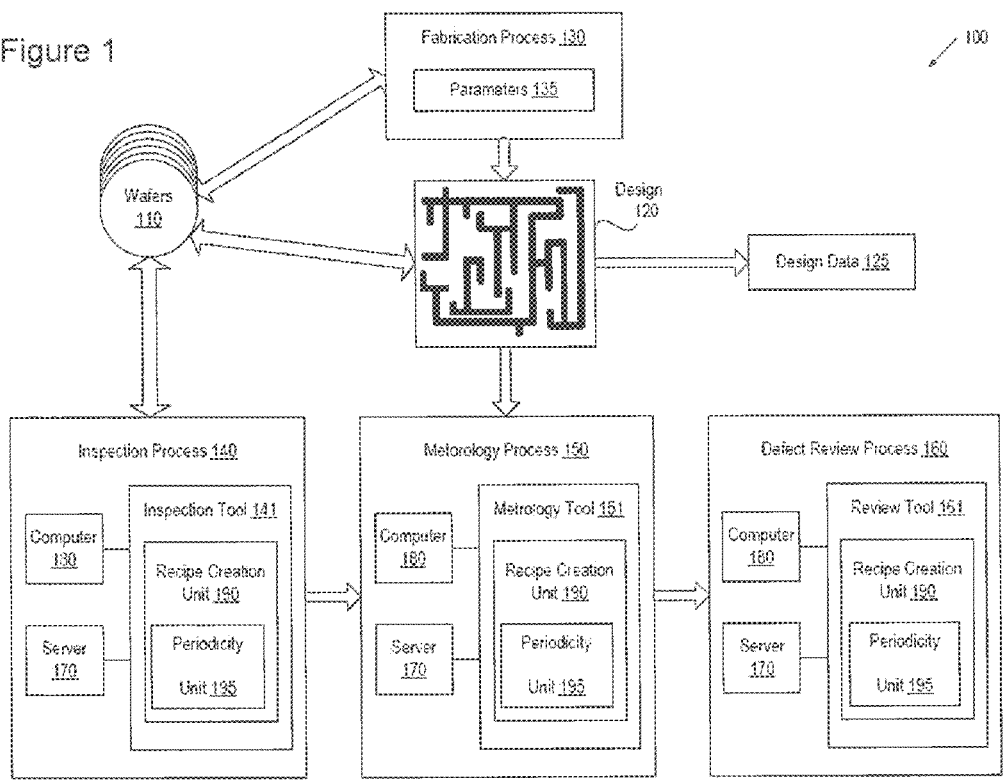
FIG. 1 illustrates an exemplary workflow for specimen design and fabrication, in accordance with embodiments of the invention.

Embodiments of the invention are directed to a method and system for creating a recipe for a manufacturing tool based on design data. Among advantages of embodiments disclosed in the currently presented subject matter is enhancing reliability of recipe creation along with significantly reducing the amount of processing time and the resources used to generate a recipe. Rather than waiting for a wafer to be produced and examining and gathering data from a produced wafer, embodiments analyze design data to identify repetitive areas in the design data. For example, the results from identifying repetitive areas in the design data can be used to determine whether to inspect a wafer or parts thereof using a cell-to-cell approach and/or a die-to-die approach. Analysis of the design data can be done offline from a manufacturing process and/or in parallel to a manufacturing process. Embodiments enable a decision of whether to perform die-to-die inspection or cell-to-cell inspection to be made in an automatic manner by basing the decision on design data, rather than on data that is derived directly from a produced wafer.

In accordance with certain aspects of the presently disclosed subject matter, there is provided a computer-implemented method of creating a recipe for a manufacturing tool. The method comprises: upon obtaining data characterizing periodical sub-arrays in one or more dies, generating candidate stitches; identifying one or more candidate stitches characterized by periodicity characteristics satisfying, at least, a periodicity criterion, thereby identifying periodical stitches among the candidate stitches; aggregating the identified periodical stitches and the periodical sub-arrays into periodical arrays, said periodical arrays to be used for automated recipe creation.

In accordance with other aspects of the presently disclosed subject matter, there is provided a computerized system for use in conjunction with creating a recipe for a manufacturing tool. The system comprises a processor; a memory accessible by the processor, said memory storing machine instructions that cause the processor to perform the following functions:
  upon obtaining data characterizing periodical sub-arrays in one or more dies, generating candidate stitches;
  identifying one or more candidate stitches characterized by periodicity characteristics satisfying, at least, a periodicity criterion, thereby identifying periodical stitches among the candidate stitches;
  aggregating the identified periodical stitches and the periodical sub-arrays into periodical arrays, said periodical arrays to be used for automated recipe creation.

In accordance with further aspects and, optionally, in combination with other aspects of the presently disclosed subject matter, generating candidate stitches can comprise identifying pairs of neighboring periodical sub-arrays matching a proximity criterion and characterized by compatible periodicity in a selected direction; and generating for each such identified pair of neighboring periodical sub-arrays a rectangle defining respective candidate stitch area.

In accordance with further aspects and, optionally, in combination with other aspects of the presently disclosed subject matter, a pair of periodical sub-arrays can be characterized by compatible periodicity in a given direction if max{C1,C2} is divisible by min{C1,C2} (i.e. Max {C1,C2}=Min{C1, C2}*N, where N is an integer number), where C1 and C2 are, respectively, periodicity values characterizing said periodical sub-arrays in said given direction. Alternatively, a pair of periodical sub-arrays can be characterized by compatible periodicity in a given direction if the least common multiple (LCM) of periodicity values characterizing said sub-arrays in said given direction are below a predefined threshold.

A candidate stitch area can satisfy the periodicity criterion if characterized in a given direction by a periodicity value Cs=K*LCM, where the multiplier K is a positive integer number and LCM is the least common multiple of periodicity values characterizing the respective neighboring periodical sub-arrays in said given direction.

In accordance with further aspects and, optionally, in combination with other embodiments of the presently disclosed subject matter, a periodical stitch can satisfy a fragmentation criterion if a number of periodical fragments in the periodical stitch is less than a fragmentation threshold and a size of each fragment in the respective direction is not less than a fragment size threshold.

In accordance with further aspects and, optionally, in combination with other aspects of the presently disclosed subject matter, aggregating into periodical arrays can comprise: associating the sub-arrays in each said identified pair into a linked sub-array; generating a maximal periodical group comprising one or more sub-arrays and stitches therebetween, wherein said group is characterized by that any pair of neighboring sub-arrays in the group is a linked sub-array with periodical stitches therebetween, and all such sub-arrays are included in said group; obtaining one or more non-overlapping uniformed maximal periodical groups; and aggregating sub-arrays and periodical stitches belonging to the same uniformed maximal periodical group into a single aggregated periodical array and assigning to this array the periodicity value characterizing the respective group.

DETAILED DESCRIPTION OF EMBODIMENTS

Referring to FIG. 1, there is illustrated an exemplary workflow for specimen design and fabrication, in accordance with embodiments of the presently disclosed subject matter. The term "specimen" used in this specification should be expansively construed to cover any kind of wafer, reticle and other structures, combinations and/or parts thereof used for manufacturing semiconductor integrated circuits, magnetic heads, flat panel displays, and other thin film devices. For purpose of illustration only, the following description is provided with respect to inspection of semiconductor wafers. Embodiments are applicable to other manufacturing operations and other specimens.

As illustrated, wafers 110 can be produced in accordance with a design 120, via a fabrication process 130 controlled by a set of process parameters 135. The design 120 can be stored, for example, in a CAD library in a data store. The design 120 can include a computer automated design (CAD) model for a specimen, for example, in a graphics form (such as GDS-II, OASIS and the like). The process parameters 135 can include a wide variety of parameters, for example, lithography parameters, etch parameters, and any other type of parameters. A data store can be a persistent storage unit. A persistent storage unit can be a local storage unit or a remote storage unit. Persistent storage units can be a magnetic storage unit, optical storage unit, solid-state storage unit, or any other suitable storage unit. Persistent storage units can be a monolithic device or a distributed set of devices.

The wafers 110 can undergo one or more manufacturing processes using one or more manufacturing tools. Examples of manufacturing processes can include, and are not limited to, a fabrication process 130, an inspection process 140, a metrology process 150, and defect review process 160, etc. Examples of manufacturing tools can include, and are not limited to, an inspection tool 141, a metrology tool 151, a defect review tool 161, tools for the fabrication process, etc.

As part of the inspection process 140, an inspection tool 141 can identify locations of defects in the wafers 110. The inspection process 140 can be performed using any suitable defect inspection system, such as, by way of non-limiting example, a Dark Field, Bright Field or E-Beam inspection system. While shown as a separate process in FIG. 1, the inspection process 140 can be performed, in some cases, inline with the fabrication process 130. As part of a metrology process 150, a metrology tool 150 can perform wafer measurement, such as measuring wafer bow, resistivity, wrap, site, flatness, thickness, etc. A metrology tool 150 can be used for testing, but can have other applications such as, for example, monitoring environmental parameters and provision of real-time data on acoustics, vibrations, and temperature in the lab. A metrology tool 151 can perform other tasks, such as, for example, holding, joining, separating, soldering, etc. An automated defect review process 160 can include a review tool 161 to process defect data in an effort to extract information that may be used to gain insight into the design process. For example, the automated defect review process 160 may extract information leading to modifications to improve the design data 120 or adjusting the fabrication process 130 to improve the processes.

The inspection process 140 can identify the defects for the review process 160. Various inspection tools 141 can be utilized, including those in which a view of a wafer 110 (or other device or object) is compared to one or more reference views. Wafers 110 can be inspected using die-to-die comparison or cell-to-cell comparison.

Figure 2:
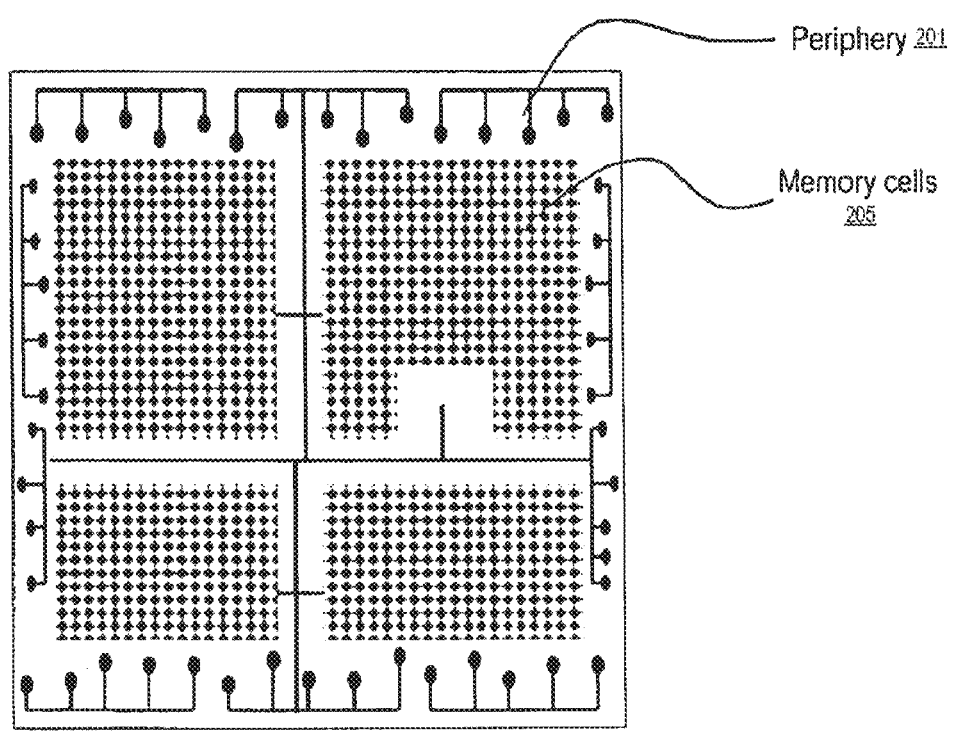
FIG. 2 is a diagram illustrating an exemplary component that can comprise one of many dies in a wafer.

An image of a wafer 110 may be obtained and the cells or dies shown therein can be inspected using any combination of appropriate die-to-die or cell-to-cell inspection/review methods. For instance, an example of a component that may be included in a wafer 110 is shown in FIG. 2. For instance, the component shown in FIG. 2 may comprise one of many dies in a wafer 110. The component may include areas that are best inspected using die-to-die inspection/review (e.g. the periphery 201 area which can comprise, for example, logic components). Such areas may be checked for defects by comparison to one or more reference dies.

However, in other situations, cell-to-cell inspection/review may be desired. For example, the device shown in FIG. 2 includes a number of (ideally) identical memory cells 205 of one or more types in the interior. For such cells 205, cell-to-cell inspection/review may be preferable since adjacent or nearby cells within the same die may be more similar than cells between adjacent dies. The similarities may be due to process conditions and/or the inspection or review tools. For instance, differences due to illumination, focus, or other optical irregularities may be less pronounced within a die as compared to between dies.

Returning to FIG. 1, the manufacturing process (and/or parts thereof) is provided in accordance with a manufacturing recipe (e.g., inspection recipe, defect review recipe, etc.). As part of creating a recipe for a given wafer or layer of a wafer, a recipe can designate different areas of the wafer to different types of inspection, review, etc. By way of non-limiting example, a recipe can designate areas as masked regions, die-to-die inspection/review regions, or cell-to-cell inspection/review regions. By way of non-limiting example, cell-to-cell inspection (i.e. inspection provided to periodical die areas with periodicity less than dies) can be preferable when adjacent or nearby areas within the same die are more similar than areas belonging to different dies. Some areas of a given wafer (e.g., periphery area comprising logic components) can be preferably inspected/reviewed using a die-to-die method. Certain areas of wafers can be inspected using any appropriate combination of die-to-die and/or cell-to-cell inspection/review methods.

Regions of the wafer can be designated to a certain type of inspection/review or other operations in accordance with images (e.g., SEM images) of a semiconductor structure that are obtained using a manufacturing tool and/or based on non-image data, such as, for example, wafer design specifications.

In one embodiment, one or more manufacturing tools (e.g., inspection tool 141, metrology tool 151, review tool 161, etc.) can include a recipe creation unit 190 to generate a manufacturing recipe. In another embodiment, one or more computers 180 can include the recipe creation unit 190 to generate a recipe for inspecting a wafer 110. The recipe creation unit 190 is further detailed with reference to FIG. 3. A computer 180 can be coupled to one or more manufacturing tools (e.g., inspection tool 141, metrology tool 151, review tool 161, etc.). In one embodiment, a computer 180 communicates to the one or more tools via a network. In another embodiment, one or more servers 170 can include a recipe creation unit 190. A server 170 can be coupled to one or more manufacturing tools. A server 170 can be hosted by any type of computing device including server computers, gateway computers, desktop computers, laptop computers, hand-held computers or similar computing device. In one embodiment, the server 170 communicates to the one or more tools via a network (not shown). The network can be a local area network (LAN), a wireless network, a mobile communications network, a wide area network (WAN), such as the Internet, or similar communication system.

As part of generating an inspection/review recipe comprising cell-to-cell inspection, there is a need to recognize respective die partitions, i.e. to identify repetitive pattern areas and repetitiveness parameters thereof. In accordance with certain embodiments of the presently disclosed subject matter, the recipe creation unit 190 can include a periodicity unit 195 operative to use design data 125 to identify periodical areas in the design data 125 for a wafer and a recipe can be generated based on the identified periodical areas for a wafer. The design data 125 can be, also, derivatives of data that is stored in a CAD library and can be in a different format than the data that is stored in a CAD library. The design data 125 can be stored in a data store coupled to the recipe creation unit 190.

The term "manufacturing recipe" or "recipe" used in the specification should be expansively construed to cover any settings of parameters specifying operation of one or more manufacturing tools (e.g. region-of-interest to be inspected, its location and repeat period on the wafer, the pixel size, beam current, charging conditions and image acquisition conditions, defect detection algorithm, image processing parameters, and/or others).

The term "design data" used in the specification should be expansively construed to cover any data indicative of hierarchical physical design (layout) of a specimen and/or data derived from the physical design (e.g. through complex simulation, simple geometric and Boolean operations, etc.). Design data (e.g., design data 125 in FIG. 1) can be provided in different formats as, by way of non-limiting example, GDSII format, OASIS format, etc. Design data specify structural elements of a certain design. A structural element can be constructed as geometrical shapes optionally combined with insertion of other structural elements. By way of non-limiting example, a given structural element can comprise one or more STRUCTURE elements inserted by means of SREF, AREF directives in GDSII format, or can comprise one or more CELL elements inserted by means of PLACEMENT and REPETITION (OASIS format). For purpose of illustration only, the following description is provided with respect to structural elements characterized by an external rectangular boundary respectively parallel to an X and Y axis whose location (referred to hereinafter as an anchor point) is selected as being in the low left corner of the rectangle. Those versed in the art will readily appreciate that the teachings of the presently disclosed subject matter are, likewise, applicable to other external boundaries, and/or other selection of anchor points. In the embodiments of the currently disclosed subject matter, geometrically identical elements with different names can be referred to as the same structural elements.

The terms "repetitive pattern area", repetitive area", "periodical pattern area" or "periodical area" used in the specification should be equally and expansively construed to cover any die area where the pattern is invariant under shift transformation with some shift value, i.e. is periodical regarding some periodicity value(s).

In accordance with certain embodiments of the presently disclosed subject matter, the periodical area can be identified with respect to one or more structural elements or derivatives thereof specified in design data. Such periodical areas are referred to hereinafter as "periodical sub-arrays". By way of non-limiting example, periodical sub-array can be defined as a rectangular area inside of a periodical M×N array, where periodical M×N array can be defined as minimal rectangular area bounding a set of instances of the structural elements specified in the design data, wherein coordinates of anchor points of the respective instances satisfy a repetitiveness criterion. For example, the repetitiveness criterion can be defined as follows: $(Xm,Yn)=(Xo,Yo)+(m*StepX, n*StepY)$, where $(Xm,Yn)$ and $(Xo,Yo)$ are coordinates of respective anchor points in a coordinate system of the above rectangular area; $m=0, 1, \ldots, M-1; n=0, 1, \ldots, N-1$; and repetitiveness parameters StepX and StepY are positive constants, representing periodicity values, correspondingly in X and Y directions.

However, stitch areas separating neighboring periodical sub-arrays can also be periodical with periodicity value equal to or multiple to the sub-array's periodicity. Aggregating, when possible, neighboring periodical sub-arrays and corresponding separating stitches into bigger periodical areas can enable wider usage of inspection/review algorithms based on periodicity of inspected/reviewed areas.

Figure 3:
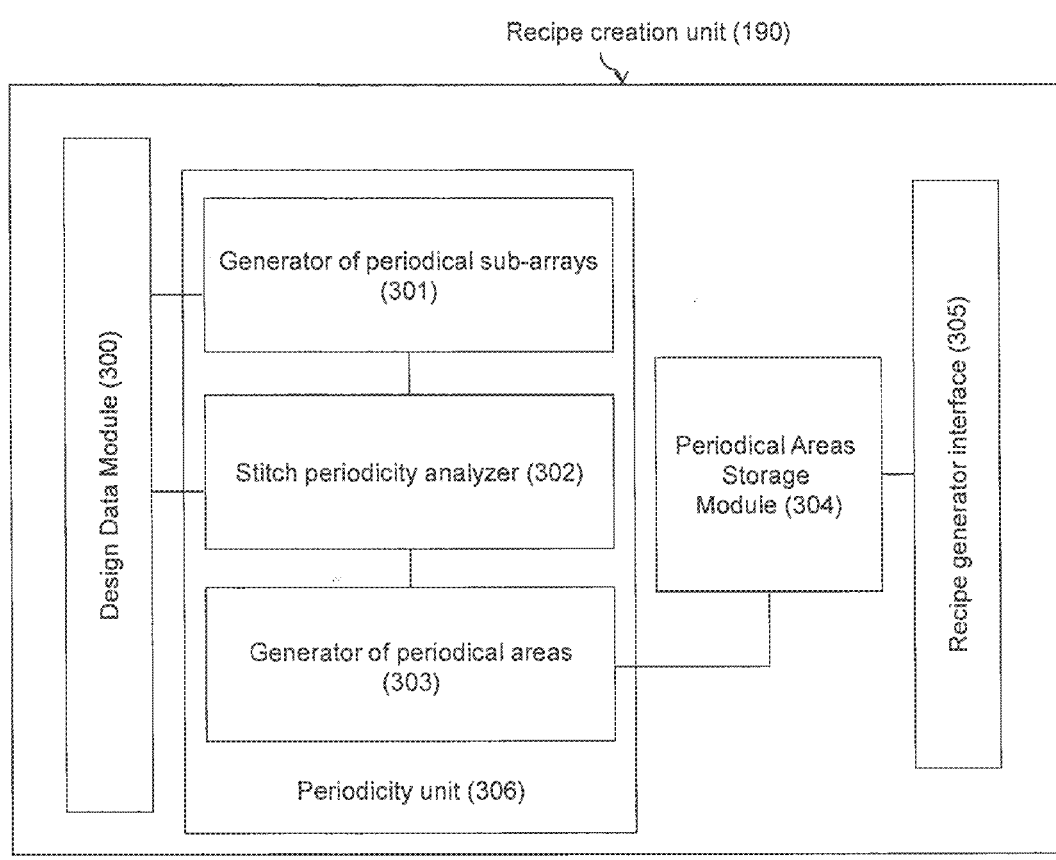
FIG. 3 illustrates a schematic functional diagram of a recipe creation unit in accordance with certain embodiments of the presently disclosed subject matter.

FIG. 3 is a generalized functional block diagram of one embodiment of a recipe creation unit in accordance with the presently disclosed subject matter. The recipe creation unit 190 comprises a design data module 300 configured to obtain and handle design data, to provide, when necessary, transformation of design data (e.g., data in CAD library) coordinates and other processing of design data required as an input for creating a recipe using design data. The design data module 300 is operatively coupled to a periodicity unit 306 operatively coupled to a storage module 304. The periodicity unit 306 comprises a processor executing functions of a generator of periodical sub-arrays 301, a stitch periodicity analyzer 302 and a generator of periodical areas 303.

By way of non-limiting example, the generator of periodical sub-arrays 301 can identify periodical sub-arrays based on design data as detailed in U.S. application Ser. No. 13/230, 483 filed Sep. 22, 2011, assigned to the assignee of the presently disclosed subject matter and incorporated hereto by reference in its entirety. Alternatively or additionally, the generator of periodical sub-arrays can obtain a set of periodical sub-arrays or part thereof from the storage module 304 and/or from a source external to the recipe creation unit.

The stitch periodicity analyzer 302 is operative to identify periodical stitches as further detailed with reference to FIGS. 4-12. The generator of periodical areas 303 is operative to aggregate the identified periodical stitches with respective neighboring periodical sub-arrays thus generating aggregated periodical areas as further detailed with reference to FIGS. 4-12.

The storage module 304 is operative to store data necessary for operation of modules 301-303 and of the entire unit 306, as well as to accommodate data characterizing the generated periodical areas. The storage module 304 is further operatively coupled to a recipe generator interface 305 enabling using the generated periodical area for further computerized recipe generation. By way of non-limiting example, the recipe generation interface can provide necessary rounding and/or multiplication of periodicity values in order to match requirements of a manufacturing tool (e.g., an inspection tool) and/or manufacturing process (e.g., inspection process).

Those versed in the art will readily appreciate that the teachings of the presently disclosed subject matter are not bound by the system illustrated in FIG. 3, equivalent and/or modified functionality can be consolidated or divided in another manner and can be implemented in any appropriate combination of software, firmware and hardware. The periodicity unit can be configured as a standalone tool to be used in conjunction with manufacture of a specimen or can be, at least partly, integrated with, for example, inspection equipment and/or metrology equipment and/or defect review equipment, etc. In one embodiment, initial die partitioning into periodical areas can be provided off-line, and further adjusted in accordance with a metrology tool and/or metrology process requirements.

Figure 4:
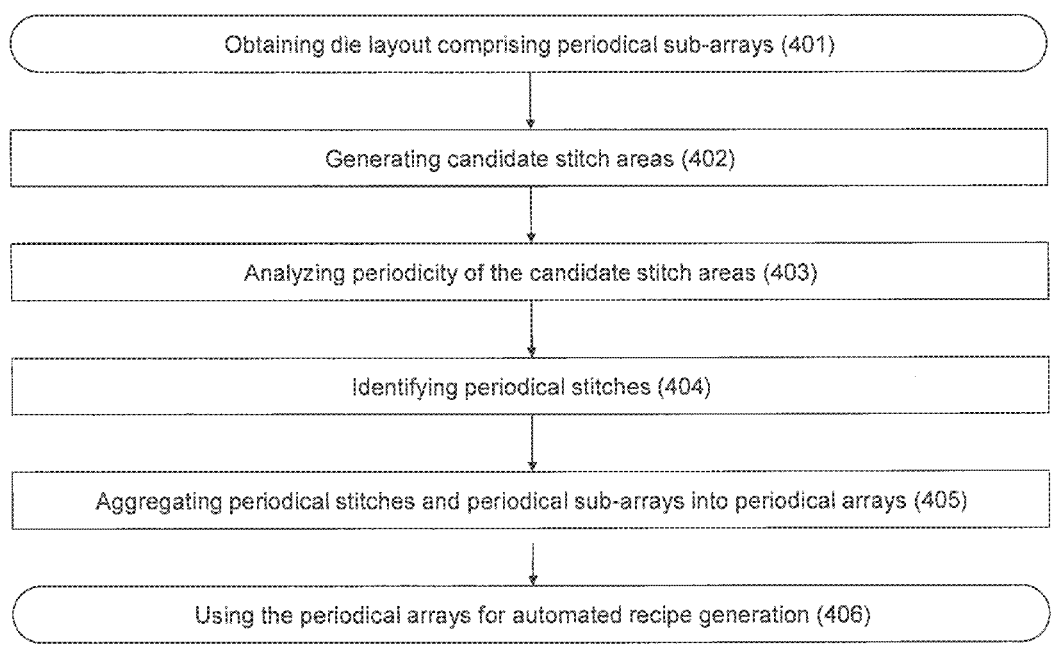
FIG. 4 illustrates a generalized flow chart of computerized recipe creation in accordance with certain embodiments of the presently disclosed subject matter.

FIG. 4 illustrates a generalized flow diagram of creating a recipe using design data in accordance with certain embodiments of the currently presented subject matter. Upon obtaining (401) data characterizing periodical sub-arrays in one or more dies (such data is referred to hereinafter as an initial die layout), the periodicity unit generates (402) candidate stitches as further detailed with reference to FIG. 5. The periodicity unit further analyzes (403) periodicity of the candidate stitches and identifies (404) periodical stitches as further detailed with reference to FIGS. 6-9. As further detailed with reference to FIGS. 10-11, the identified periodical stitches are aggregated (405) with periodical sub-arrays into aggregated periodical arrays further used (406) for automated recipe creation. The aggregated periodical arrays constitute a set of rectangles inside respective one or more dies, said set defining areas that can be inspected in cell-to-cell mode. For purpose of illustration only, the following description is provided for Manhattan rectangles. It is noted that the teachings of the presently disclosed subject matter are, likewise, applicable to rectangles with non-Manhattan orientation. Each rectangle is characterized by periodicity value in X and/or Y direction. Data characterizing the aggregated periodical arrays in one or more dies is referred to hereinafter as an advanced die layout.

For purpose of illustration only, the following description is provided with respect to inspection/review provided in Y direction. Those versed in the art will readily appreciate that the teachings of the presently disclosed subject matter are, likewise, applicable to other directions.

Referring to FIG. 5a, there is illustrated a schematic non-limiting example of an initial die layout for Y direction inspection/review. Rectangles 501-503 and 505-512 illustrate periodical sub-arrays characterized in Y direction by periodicity value $C_y$, and rectangle 504 illustrate a periodical sub-array characterized by periodicity value $2C_y$.

Two neighboring periodical sub-arrays can be considered as satisfying a proximity criterion in Y direction if matching the following conditions illustrated, by way of non-limiting example, in FIG. 5b:

a distance (520) in X direction between the respective neighboring rectangles is less than a distance threshold;

a ratio between a common length (521) and a length (523, 522) of any of the respective neighboring rectangles (513, 514) shall exceed a common ratio threshold characterizing overlapping between the neighboring sub-arrays in stitch direction;

a difference between the length of any of the respective neighboring rectangles and the common length shall be less than a misalignment threshold. The misalignment threshold characterizes maximal allowed difference of coordinates of two neighboring sub-arrays in stitch direction.

Referring back to FIG. 5a, in the illustrated example, the pairs of sub-arrays 502-503, 503-504, 504-505, 505-506, 506-508, 508-509, 511-512 meet the proximity criterion.

Figure 6:
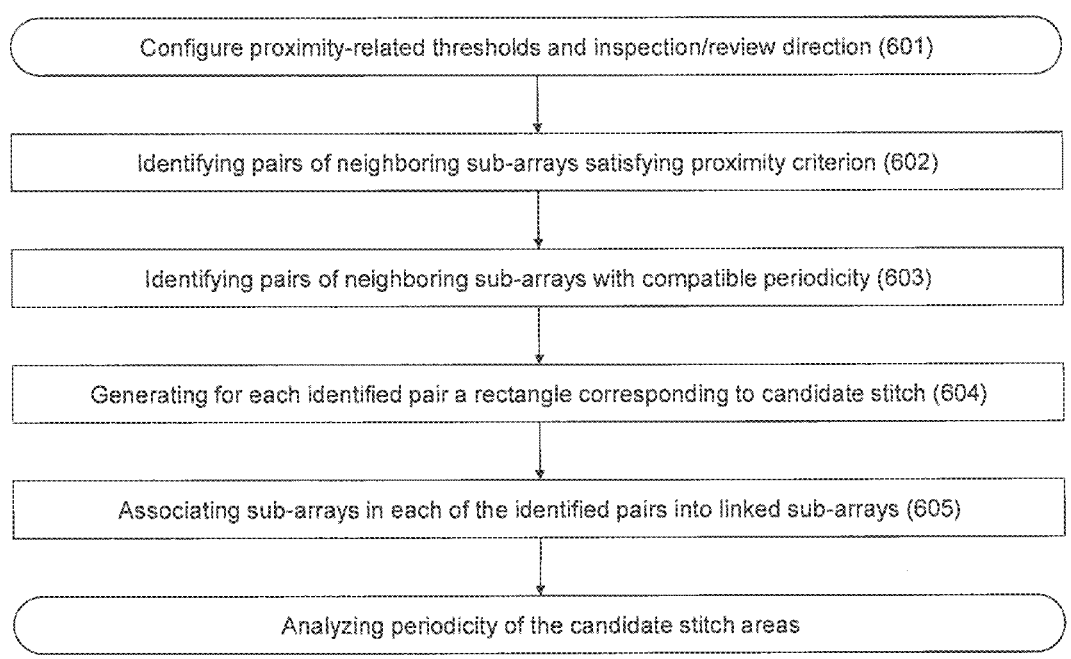
FIG. 6 illustrates a generalized flow diagram of generating candidate stitch areas in accordance with certain embodiments of the presently disclosed subject matter.

FIG. 6 illustrates a generalized flow diagram of generating candidate stitches. Upon configuring (601) proximity-related thresholds (e.g. the distance threshold, the common ration threshold, the misalignment threshold) and selecting the inspection/reviewing direction, the periodicity unit identifies (602) the pairs of neighboring sub-arrays matching the proximity criterion and further identifies (603) the pairs of neighboring sub-arrays characterized by compatible periodicity in the selected direction. Two sub-arrays can be characterized by compatible periodicity in Y direction if $\max\{C_{y1}, C_{y2}\}$ is divisible by $\min\{C_{y1}, C_{y2}\}$, where $C_{y1}$ and $C_{y2}$ are, respectively, periodicity values of $1^{st}$ and $2^{nd}$ sub-arrays. Alternatively, compatible periodicity can be defined as matching least common multiple to be below a predefined threshold, or in any other suitable way.

The periodicity unit further generates (604) for each such identified pair of neighboring sub-arrays a rectangle defining respective candidate stitch area (illustrated by rectangle 515 in FIG. 5b), and associates (605) the sub-arrays in such a pair into a linked sub-array. The boundaries of the rectangle can be defined as follows: if left sub-array is defined by the low-left (LL) vertex (x1L,y1L) and the upper-right (UR) vertex (x2L,y2L), right sub-array is defined by LL vertex (x1R,y1R) and UR vertex (x2R,y2R), then candidate stitch rectangle will be LL=(x2L,Y1), UR=(x1R,Y2), where segment [Y1,Y2] is a common part of segments [y1L,y2L] and [y1R,y2R].

Figure 7:
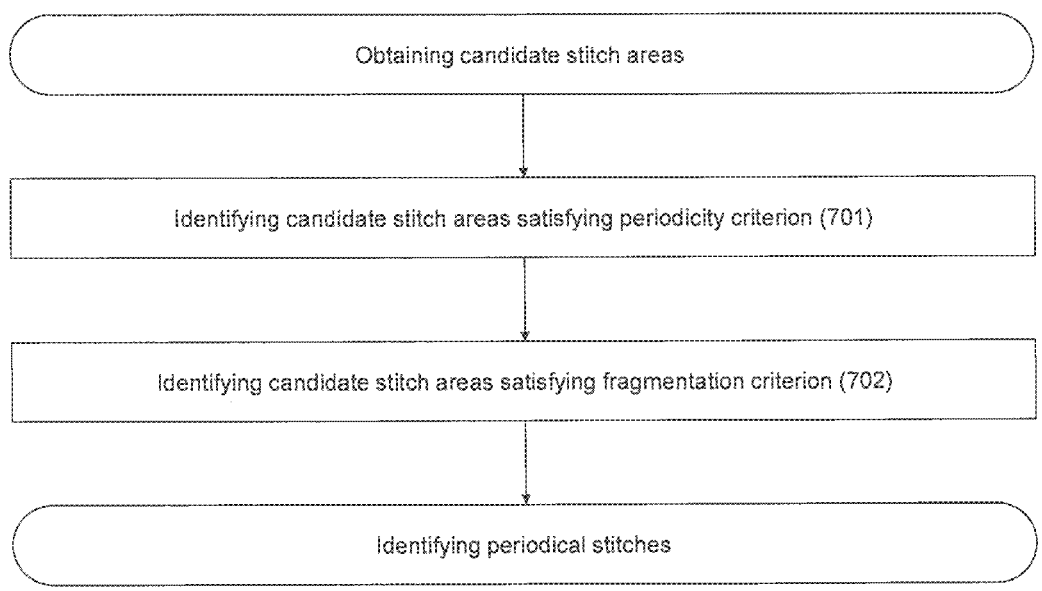
FIG. 7 illustrates a generalized flow diagram of identifying periodical stitches for further aggregation in accordance with certain embodiments of the presently disclosed subject matter.

FIG. 7 illustrates a generalized flow diagram of identifying periodical stitches for further aggregation. For further aggregation with respective pair of neighboring periodical sub-arrays with periodicities $C_{y1}$ and $C_{y2}$ into a periodical array, a stitch area shall satisfy a periodicity criterion. For example, if $\max\{C_{y1}, C_{y2}\}$ is divisible by $\min\{C_{y1}, C_{y2}\}$, such stitch area can be characterized by the periodicity value $C_s = K * \max\{C_{y1}, C_{y2}\}$, where the multiplier K is a positive integer number and the values $\max\{C_{y1}, C_{y2}\}$ and $\min\{C_{y1}, C_{y2}\}$ correspond to periodicity values in stitch direction common to the pair of sub-arrays adjacent to the stitch. In a general case, such stitch area can be characterized by the periodicity value $C_s = K * LCM$ of periodicity values of the respective sub-arrays.

The periodicity unit analyses periodicity of candidate stitches and identifies (701), among the candidate stitches, the stitch areas comprising one or more fragments satisfying the periodicity criteria; such fragments are referred to hereinafter as periodical fragments.

Figure 8:
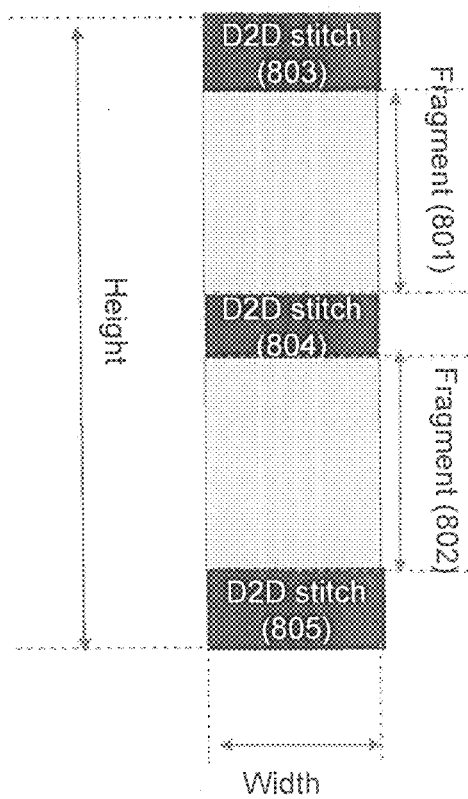
FIG. 8 illustrates a non-limiting schematic example of a stitch comprising several periodical fragments in accordance with certain embodiments of the presently disclosed subject matter.

FIG. 8 illustrates a non-limiting example of a candidate stitch area comprising several periodical fragments (illustrated as 801 and 802) divided by areas with broken periodicity (illustrated as 803, 804 and 805). It should be noted that non-periodical areas may separate periodical fragments or may be inside thereof (like islands), however, periodical area inside a candidate stitch area shall be significant enough for inspection/review tool.

By way of non-limiting example, a given candidate stitch area comprising one or more fragments satisfying the periodicity criterion can be referred to as a periodical stitch if it further satisfies a fragmentation criterion. The fragmentation criterion can be defined as follows:

a number of periodical fragments in the periodical stitch shall be less than a fragmentation threshold (in certain embodiments configured as equal to 3);

Y direction size of each fragment shall not be less than a fragment size threshold.

By way of non-limiting example, the fragment size threshold can be defined as the largest among two parameters: MinRepAlongStitch*$C_s$ and SignificRatio*height, where "height" is a size of stitch area rectangle in stitch direction, MinRepsAlongStitch (in certain embodiments configured as equal to 3) characterizes a minimal number of repetitions inside the fragment's repetitive pattern, and SignificRatio (in certain embodiments configured as equal to 0.2) is a parameter characterizing significance of the periodical area inside of the stitch.

Referring back to FIG. 7, the periodicity unit further identifies (703) stitches matching the fragmentation criterion, thereby identifying the periodical stitches.

Optionally, an empty stitch area can be considered as a periodical stitch with periodicity $C_s$=LCM (note that $C_s=\max\{C_{y1}, C_{y2}\}$ if $\max\{C_{y1}, C_{y2}\}$ is divisible by $\min\{C_{y1}, C_{y2}\}$).

Figure 9:
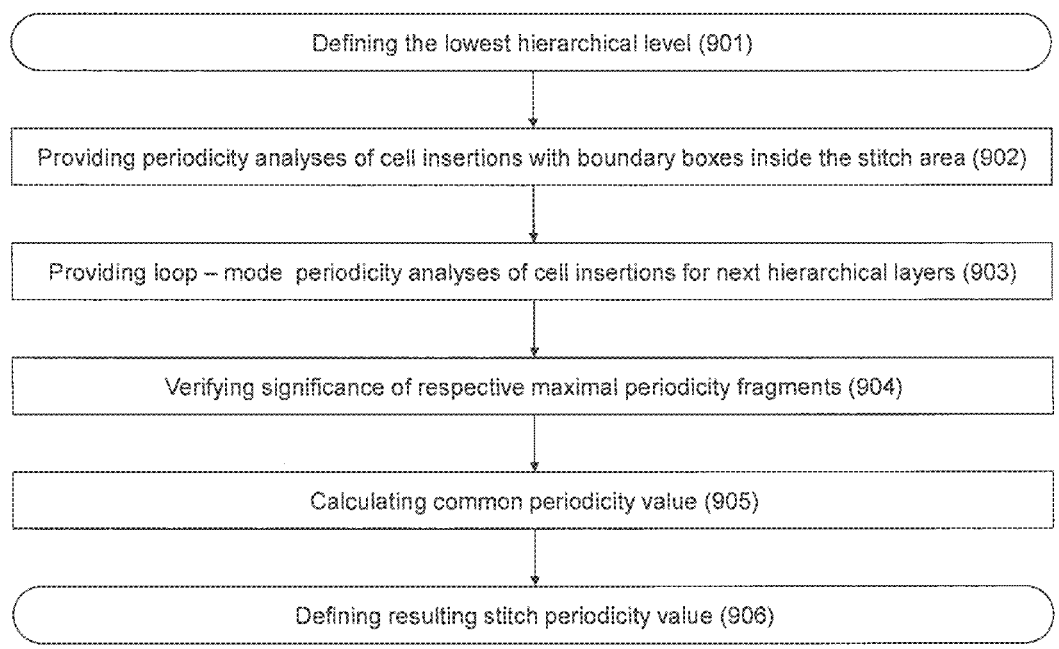
FIG. 9 illustrates a generalized flow diagram of identifying periodical stitches with the help of insertion-point analyses in accordance with certain embodiments of the presently disclosed subject matter.

By way of non-limiting example, the periodical stitches can be identified with the help of periodicity analysis of insertion points of CAD cells instances, whose bounding boxes belong to the stitch area. Insertion-points analysis can reduce amount of geometrical data to be analyzed. After the analysis of insertion points has completed, remaining stitch geometry (polygons inside the stitch, not belonging to any of already analyzed CAD cells) is analyzed on periodicity regarding $_{Cs-RES}$ characterizing the stitch. FIG. 9 illustrates a generalized flow diagram of identifying periodical stitches with the help of insertion-point analyses. For a given stitch, the periodicity unit defines (901) the lowest hierarchical level (i.e. having no non-empty child cells) and provides periodicity analyses (902) of CAD cell insertions corresponding to bounding boxes totally inside the stitch area. The periodicity unit further provides loop-mode periodicity analyses (903) of CAD cell insertions for the next hierarchical layers. At each step the periodicity analysis is provided for a next hierarchical layer having child cells only from previously analyzed hierarchical layers. The analysis is provided for cell insertions corresponding to bounding boxes totally inside the stitch area, comprising at least one polygon not belonging to any of the child cells.

The periodicity unit further analyses cell insertions defined at Steps 901-903, and verifies (904) significance of the respective maximal periodicity fragment. If the fragment is not significant, the periodicity unit is looking for a parent cell inside the stitch area containing periodicity fragment satisfying significance criterion.

The periodicity unit further calculates (905) common periodicity value $C_{com}$ for all defined cell insertions and finds common periodicity fragments. By way of non-limiting example, the generator of periodical sub-arrays 301 can identify periodical sub-arrays and calculate the common periodicity value based on design data as detailed in U.S. application Ser. No. 13/230,483 filed Sep. 22, 2011, assigned to the assignee of the presently disclosed subject matter and incorporated hereto by reference in its entirety. The periodicity unit further analyses remaining polygons (not belonging to any analyzed cell insertions) inside the fragments on periodicity with value $C_{com}$, finds final periodicity fragments and defines (906) resulting stitch periodicity value $C_{s\text{-}RES}$ characterizing the stitch.

Figure 10:
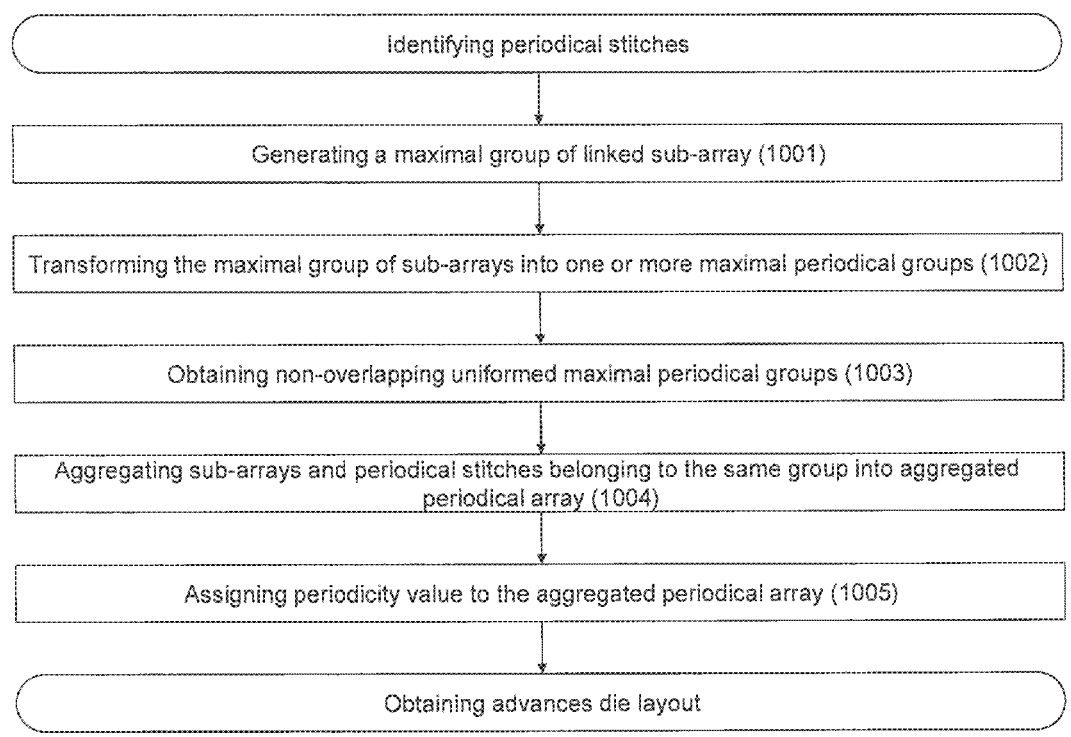
FIG. 10 illustrates a generalized flow diagram of aggregating the identified periodical stitches with respective sub-arrays in accordance with certain embodiments of the presently disclosed subject matter.

A generalized flow diagram of aggregating the identified periodical stitches with respective sub-arrays is illustrated in FIG. 10. FIGS. 11*a*-11*f* schematically illustrate different aggregating steps provided for the exemplary initial layout illustrated in FIG. 5*a*. Upon identifying periodical stitches, the periodicity unit generates (1001) a maximal group of linked sub-arrays, i.e. a group characterized by that any pair of neighboring sub-arrays in the group are linked sub-arrays, and all such sub-arrays are included in the group. The periodicity unit further transforms (1002) the maximal group of linked sub-arrays into one or more maximal periodical groups. Maximal periodical groups are constituted by sub-arrays of the maximal group of linked sub-arrays and stitches therebetween, wherein the stitch between each pair of linked sub-arrays in the maximal periodical group is periodical. Optionally, a maximal periodical group can be also constituted by a single sub-array formerly comprised in the maximal sub-arrays group. In the non-limiting example illustrated in FIGS. 11*a*-11*b* the stitch 1102 is not periodical, and the maximal group 1101 has been transformed into maximal periodical groups 1103 and 1104 (containing a single sub-array).

The periodicity unit further analyzes periodicity values of all sub-arrays inside each maximal periodical group. If a given maximal periodical group comprises sub-arrays with different periodicity values, the periodicity unit transforms (1003) the given maximal periodical group into one or more non-overlapping uniformed maximal periodical groups. A maximal periodical group is considered as uniformed if periodicity values of all sub-arrays comprised within the group match a uniformity criterion. By way of non-limiting example, the uniformity criterion can require that maximal periodical value of all sub-arrays is divisible by all other periodicity values; or the uniformity criterion can require that LCM of all sub-arrays is below a predefined threshold, etc. In some cases different periodicity values of sub-arrays may indicate different nature and, respectively, different inspection parameters of the sub-arrays. Thus, it can be advantageous to generate the uniformed maximal periodical groups characterized by equal periodicity values of all sub-arrays comprised within each of the uniformed groups.

In the non-limiting example further illustrated in FIG. 11*c*, periodicity of sub-array 1105 is $2*C_y$, while the periodicity of adjacent sub-arrays 1106 and 1107 is $C_y$, and these arrays satisfy the proximity criterion. In such a case, the sub-array 1105 is transformed into a candidate stitch area and further transformed into a periodical stitch 1108 characterized by periodicity value $_{Cs}=2*C_y$, and the sub-arrays 1106 and 1107 are associated in linked sub-array. Thus, the resulting uniformed maximal periodical group 1109 comprises linked sub-arrays with equal periodicity. Alternatively, the maximal periodical group 1103 can be split in several uniformed sub-groups, each constituted by sub-arrays with equal periodicity.

Upon obtaining uniformed maximal periodical groups, the periodicity unit aggregates (1004) sub-arrays and periodical stitches belonging to the same uniformed maximal periodical group into a single aggregated periodical array and assigns (1005) to this array a periodicity value common to all aggregated sub-arrays and periodical stitches. The aggregated periodical array is characterized by an aggregated bounding box, i.e. the bounding box of all sub-arrays constituting the respective group.

The disclosed way of generation of the candidate stitches guarantees that periodical stitches belonging to the group are always inside the aggregated bounding box. However, the boundaries of sub-arrays converted into stitch when obtaining uniformed periodical maximal areas are not necessarily inside the aggregated bounding box and, hence, can be cropped by the aggregating rectangle.

In case of non-zero misalignment threshold, one or more sub-arrays in the unified maximal periodical group can overlap with another sub-array of the initial die layout, said array external to the group (e.g. sub-array 1110 illustrated in FIG. 11*d*). In order to avoid overlapping of aggregated periodical arrays, the periodicity unit further analyses such potential over-lapping and splits, if necessary, the respective unified maximal periodical group into sub-groups with no overlapping with such external arrays of the initial die layout (e.g. sub-groups 1111 and 1112 illustrated in FIG. 11*d*).

It should be noted that although periodicity values $C_y$ of the sub-arrays in a given uniformed maximal periodical group are equal, periodical stitches inside the group can be characterized by different periodicity $C_s=K*C_y$ as multipliers K can be different for different stitches. Accordingly, when assigning (1005) the periodicity value common to all aggregated sub-arrays and periodical stitches, the periodicity unit computes minimal periodicity value common to all periodical stitches inside the group. If such computed minimal common periodicity value is more than a predefined threshold, the periodicity unit can split the uniformed maximal periodical group into two sub-groups along the stitch area (e.g. with the biggest periodicity value). In the non-limiting example illustrated in FIG. 11*e* the group 1111 is split into sub-groups 1113 and 1114 along the stitch 1115 with the biggest periodicity value.

Figure 11A:
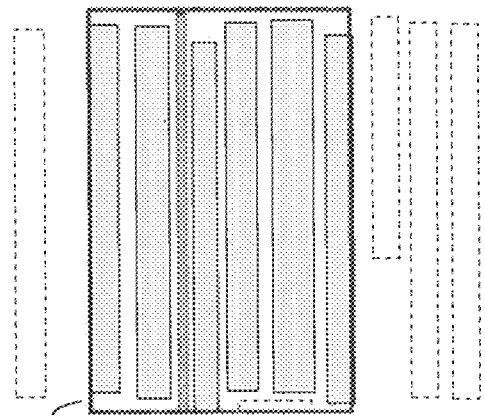
Figure 11B:
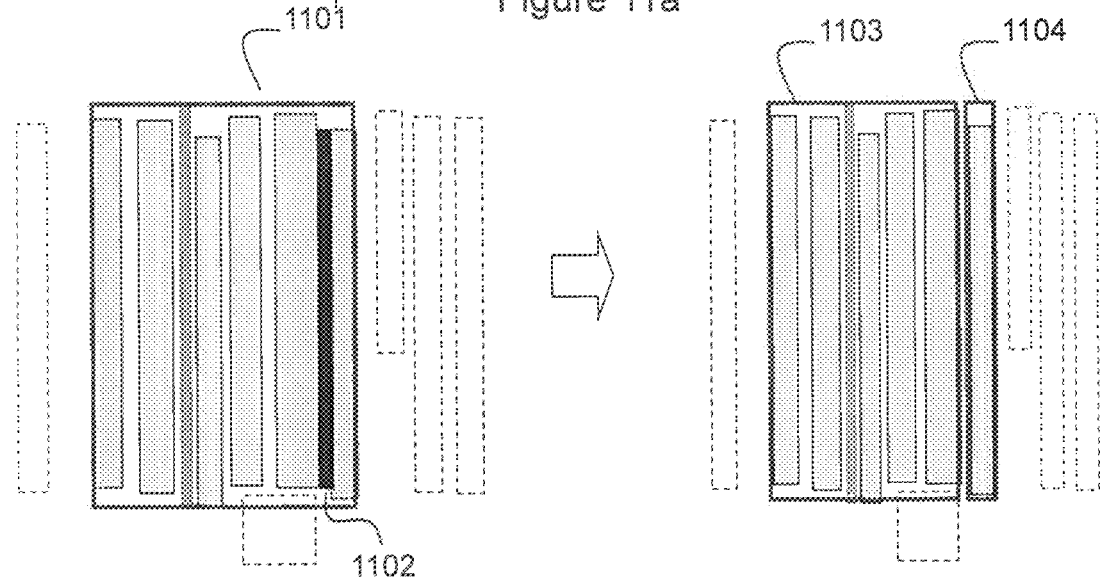
Figure 11E:
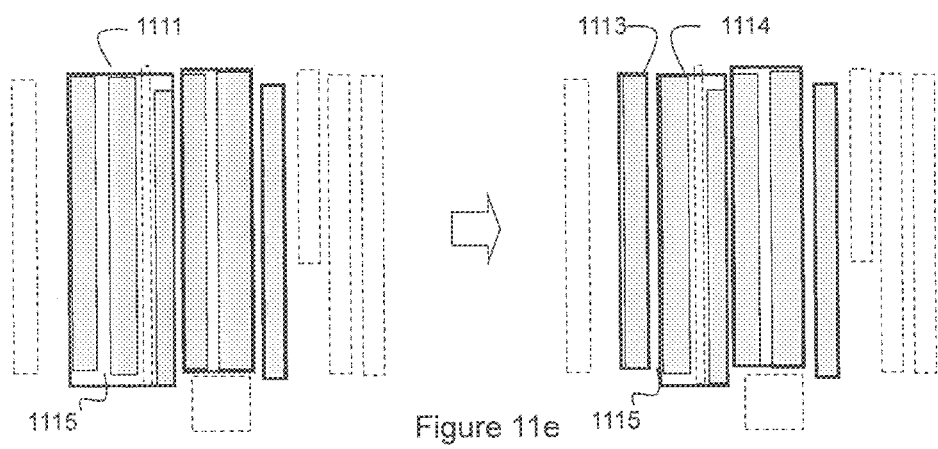
Figure 11F:
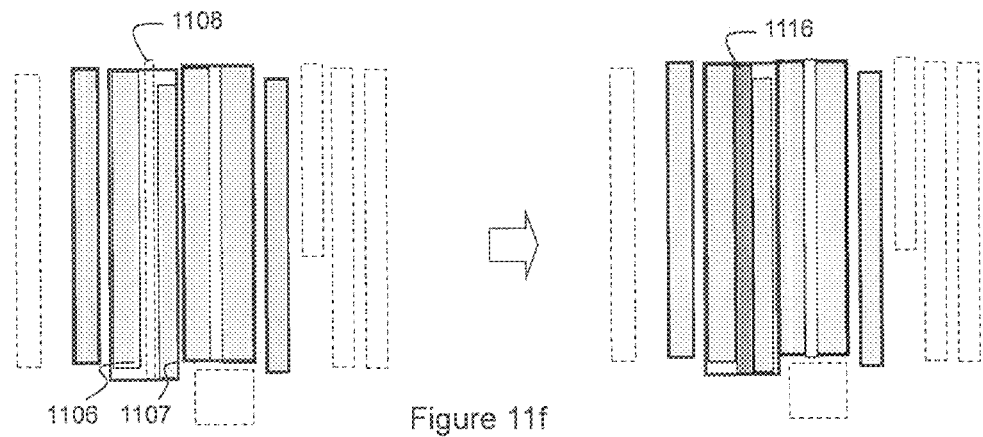

FIG. 11*f* illustrates a non-limiting example where, resulting from conversion of sub-array into stitch 1108, the stitch area between sub-arrays 1106 and 1107 is constituted by rectangles with different periodicity values. These stitch rectangles can be aggregated into joint stitch rectangle 1116 characterized by periodicity value recomputed as minimal periodicity value common for all adjacent periodical rectangles within the stitch.

Figure 12A:
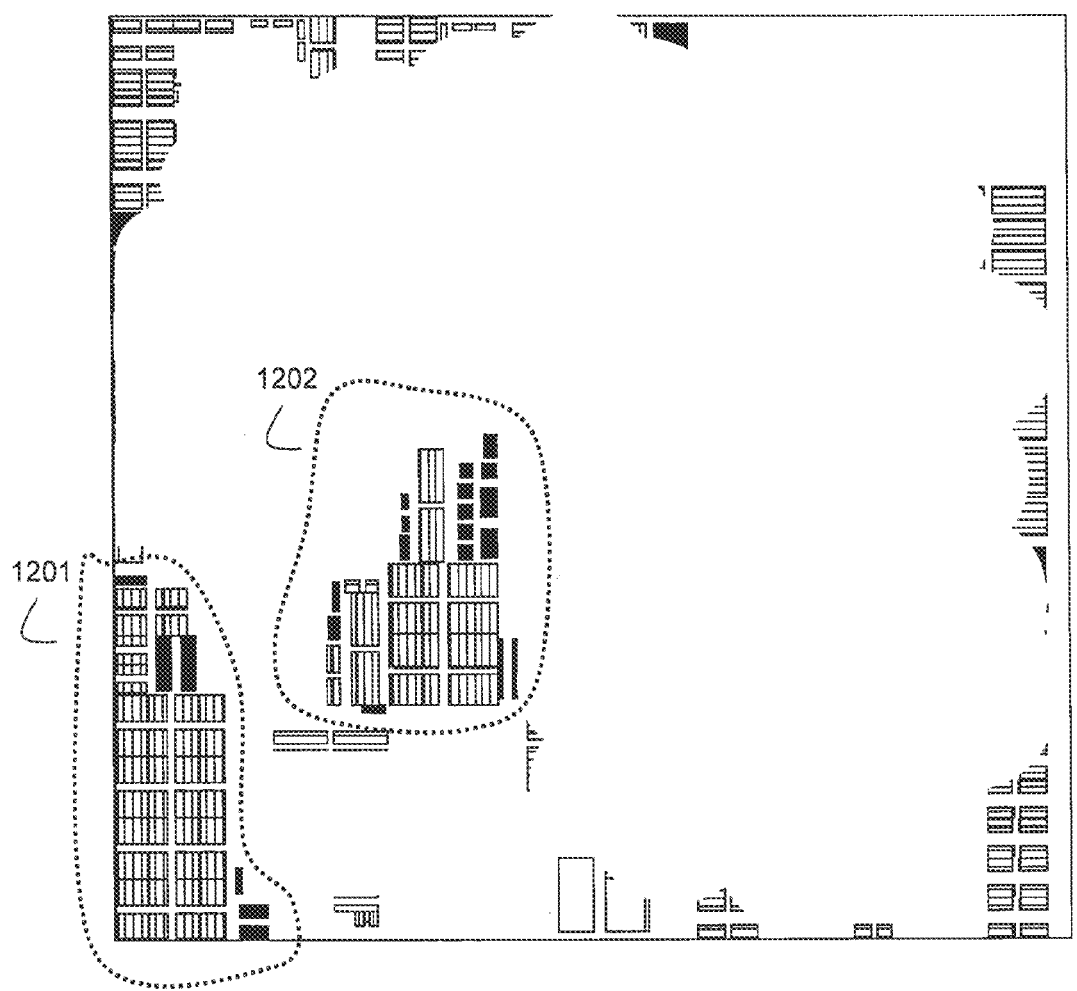
FIGS. 12a-12b illustrate non-limiting examples of experimental initial die layout and advanced die layout for CAD SRAM file with Y direction of inspection.
Figure 12B:
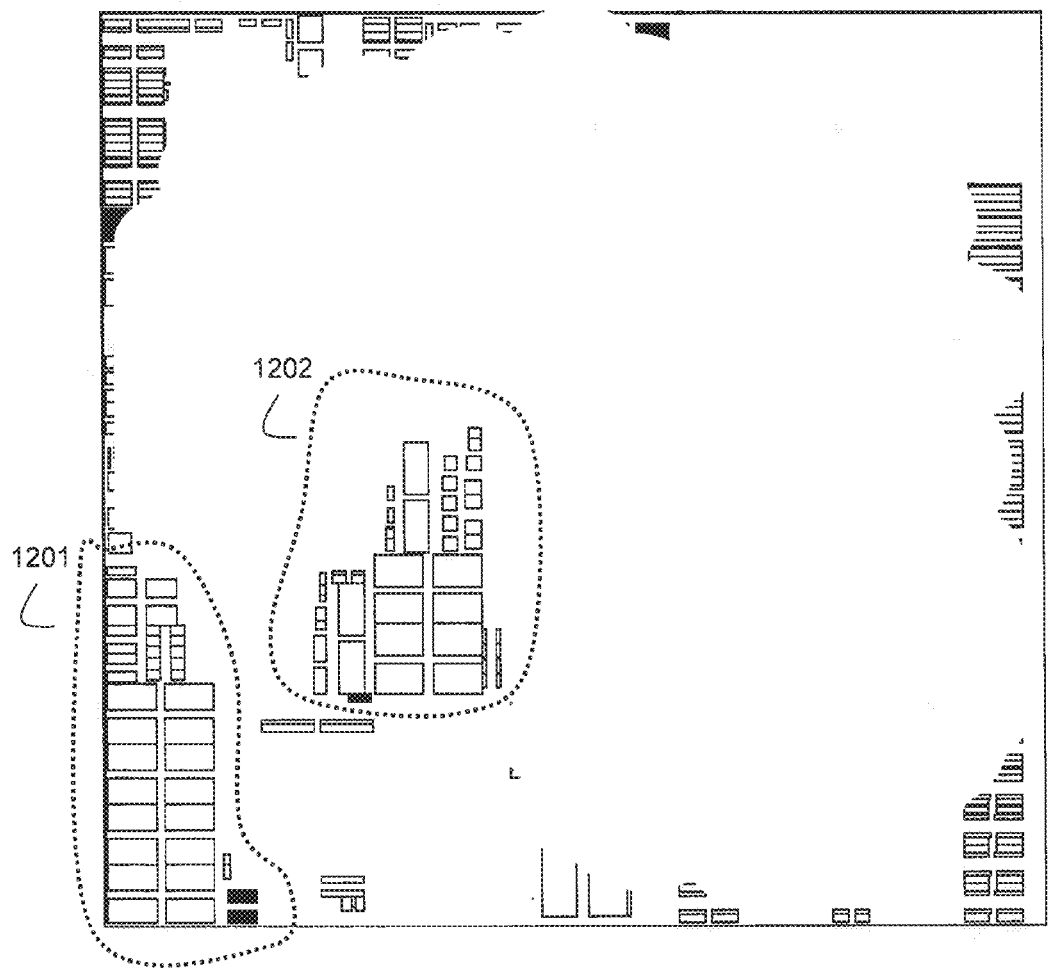

FIG. 12*a* illustrates a non-limiting experimental example of initial die layout for CAD SRAM file with Y direction of inspection. FIG. 12*b* illustrates an advanced die layout for the same file, said layout obtained in accordance with certain embodiments of the currently presented subject matter. As illustrated, relatively small periodical sub-arrays in the initial die layout (e.g. within areas 1201 and 1202) have been aggregated into larger periodical areas suitable for cell-to-cell inspection/review.

In the above description, numerous details are set forth. It will be apparent, however, to one skilled in the art, that the presently disclosed subject matter may be practiced without these specific details. In some instances, well-known structures and devices are shown in block diagram form, rather than in detail, in order to avoid obscuring the presently disclosed subject matter.

Unless specifically stated otherwise, as apparent from the following discussions, it is appreciated that throughout the specification discussions utilizing terms such as "processing", "generating", "calculating", "identifying", "generating", "transforming", "searching", "finding", or the like, refer to the action and/or processes of a computer that manipulate and/or transform data into other data, said data represented as physical, such as electronic, quantities and/or said data representing the physical objects. The terms "computer" and "processor" should be expansively construed to cover any kind of electronic system with data processing capabilities.

The operations in accordance with the teachings herein can be performed by a computer specially constructed for the desired purposes or by a general-purpose computer specially configured for the desired purpose by a computer program stored in a non-transitory computer readable storage medium.

Embodiments of the presently disclosed subject matter are not described with reference to any particular programming language. It will be appreciated that a variety of programming languages can be used to implement the teachings of the inventions as described herein.

The term "criterion" used in this patent specification should be expansively construed to include any compound criterion, including, for example, several criteria and/or their logical combinations.

It is to be understood that the invention is not limited in its application to the details set forth in the description contained herein or illustrated in the drawings. The invention is capable of other embodiments and of being practiced and carried out in various ways. It should be noted that the invention is not bound by the specific algorithm of processing or specific structure. Those versed in the art will readily appreciate that the invention is, likewise, applicable to any other processing or presentation with equivalent and/or modified functionality that can be consolidated or divided in another manner.

It will also be understood that the invention further contemplates a machine-readable non-transitory memory tangibly embodying a program of instructions executable by the machine for executing the method of the invention.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Those skilled in the art will readily appreciate that various modifications and changes can be applied to the embodiments of the invention as hereinbefore described without departing from its scope, defined in and by the appended claims.

The invention claimed is:

1. A method comprising:
   identifying, from design data, pairs of neighboring periodical sub-arrays matching a proximity criterion and characterized by compatible periodicity in a given direction if a least common multiple of periodicity values characterizing said sub-arrays in said given direction is below a predefined threshold, wherein the design data characterizes periodical sub-arrays in one or more dies;
   generating for each identified pair of neighboring periodical sub-arrays a rectangle defining a respective candidate stitch;
   identifying periodical stitches among the candidate stitches;
   aggregating, by a computer, the periodical stitches and the periodical sub-arrays to create periodical arrays; and
   causing a recipe to be generated using the periodical arrays created based on the design data.

2. The method of claim 1, wherein a pair of periodical sub-arrays is characterized by compatible periodicity in a given direction if max {C1,C2} is divisible by min{C1,C2}, where C1 and C2 are, respectively, periodicity values characterizing said periodical sub-arrays in said given direction.

3. The method of claim 1, wherein a candidate stitch satisfies the periodicity criterion if characterized in a given direction by a periodicity value Cs=K*LCM, where the multiplier K is a positive integer number and LCM is the least common multiple of periodicity values characterizing the respective neighboring periodical sub-arrays in said given direction.

4. The method of claim 1, wherein identifying periodical stitches among the candidate stitches comprises identifying within the candidate stitch areas one or more periodical fragments satisfying the periodicity criteria.

5. The method of claim 4, wherein identifying periodical stitches among the candidate stitches further comprises identifying periodical stitches satisfying a fragmentation criterion.

6. The method of claim 5, wherein a periodical stitch satisfies a fragmentation criterion if a number of periodical fragments in the periodical stitch is less than a fragmentation threshold and a size of each fragment in the respective direction is not less than a fragment size threshold.

7. The method of claim 1, wherein aggregating the periodical stitches and the periodical sub-arrays to create the periodical arrays comprises:
   associating the sub-arrays in each said identified pair into a linked sub-array;
   generating a maximal periodical group comprising one or more sub-arrays and stitches therebetween, wherein said group is characterized by that any pair of neighboring sub-arrays in the group is a linked sub-array with periodical stitches therebetween, and all such sub-arrays are included in said group;
   obtaining one or more non-overlapping uniformed maximal periodical groups; and
   aggregating sub-arrays and periodical stitches belonging to the same uniformed maximal periodical group into a single aggregated periodical array and assigning to this array the periodicity value characterizing the respective group.

8. The method of claim 7 wherein the non-overlapping uniformed maximal periodical groups are characterized by periodicity values equal to all sub-arrays in a respective group.

9. A system comprising:
   a processor;
   a memory accessible by the processor, said memory storing machine instructions that cause the processor to perform the following functions:
      identifying, from design data, pairs of neighboring periodical sub-arrays matching a proximity criterion and characterized by compatible periodicity in a given direction if a least common multiple of periodicity values characterizing said sub-arrays in said given direction is below a predefined threshold, wherein the design data characterizes periodical sub-arrays in one or more dies;
      generating for each identified pair of neighboring periodical sub-arrays a rectangle defining a respective candidate stitch;
      identifying periodical stitches among the candidate stitches;
      aggregating the periodical stitches and the periodical sub-arrays to create periodical arrays; and
      cause a recipe to be generated using the periodical arrays created based on the design data.

10. The system of claim 9, wherein a pair of periodical sub-arrays is characterized by compatible periodicity in a given direction if max {C1,C2} is divisible by min{C1,C2}, where C1 and C2 are, respectively, periodicity values characterizing said periodical sub-arrays in said given direction.

11. The system of claim 9, wherein a candidate stitch satisfies the periodicity criterion if characterized in a given direction by a periodicity value Cs=K*max{Cy1,Cy2}, where the multiplier K is a positive integer number and where C1 and C2 are, respectively, periodicity values characterizing the respective neighboring periodical sub-arrays in said given direction.

12. The system of claim 9, wherein identifying periodical stitches among the candidate stitches comprises identifying within areas of the candidate stitches one or more periodical fragments satisfying the periodicity criteria.

13. The system of claim 12, wherein identifying periodical stitches among the candidate stitches further comprises identifying periodical stitches satisfying a fragmentation criterion.

14. The system of claim 13, wherein a periodical stitch satisfies a fragmentation criterion if a number of periodical fragments in the periodical stitch is less than a fragmentation threshold and a size of each fragment in the respective direction shall is not less than a fragment size threshold.

15. The system of claim 9, wherein aggregating the periodical stitches and the periodical sub-arrays to create the periodical arrays comprises:
   associating the sub-arrays in each said identified pair into a linked sub-array;
   generating a maximal periodical group comprising one or more sub-arrays and stitches therebetween, wherein said group is characterized by that any pair of neighboring sub-arrays in the group is a linked sub-array with periodical stitches therebetween, and all such sub-arrays are included in said group;
   obtaining one or more non-overlapping uniformed maximal periodical groups; and
   aggregating sub-arrays and periodical stitches belonging to the same uniformed maximal periodical group into a single aggregated periodical array and assigning to this array the periodicity value characterizing the respective group.

16. A non-transitory computer readable medium including instructions that, when executed by a processing system, cause the processing system to perform operations comprising:
   identifying, from design data, pairs of neighboring periodical sub-arrays matching a proximity criterion and characterized by compatible periodicity in a given direction if a least common multiple of periodicity values characterizing said sub-arrays in said given direction is below a predefined threshold, wherein the design data characterizes periodical sub-arrays in one or more dies;
   generating for each identified pair of neighboring periodical sub-arrays a rectangle defining a respective candidate stitch;
   identifying periodical stitches among the candidate stitches;
   aggregating, by the processing system, the periodical stitches and the periodical sub-arrays to create periodical arrays; and
   causing a recipe to be generated using the periodical arrays created based on the design data.

* * * * *